United States Patent
Benson

(10) Patent No.: US 10,022,557 B2
(45) Date of Patent: *Jul. 17, 2018

(54) USING A GUIDED MEMBER TO FACILITATE BRACHYTHERAPY DEVICE SWAP

(71) Applicant: Hologic, Inc., Bedford, MA (US)

(72) Inventor: Maria Benson, Boylston, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,589

(22) Filed: May 27, 2016

(65) Prior Publication Data

US 2016/0287902 A1    Oct. 6, 2016

Related U.S. Application Data

(63) Continuation of application No. 12/894,888, filed on Sep. 30, 2010, now Pat. No. 9,352,172.

(51) Int. Cl.
*A61N 5/10* (2006.01)
*A61B 5/107* (2006.01)
(Continued)

(52) U.S. Cl.
CPC .......... *A61N 5/1015* (2013.01); *A61B 5/1076* (2013.01); *A61M 25/0169* (2013.01);
(Continued)

(58) Field of Classification Search
CPC .......... A61N 5/1001–5/1016; A61M 25/0169; A61M 25/09; A61M 2025/09125;
(Continued)

(56) References Cited

U.S. PATENT DOCUMENTS 3,324,847 A    6/1967   Zoumboulis
3,502,878 A    3/1970   Stewart
(Continued)

FOREIGN PATENT DOCUMENTS

DE    2539553    3/1977
EP    0340881    10/1992
(Continued)

OTHER PUBLICATIONS

"DuPont Teflon PFA HP Plus", XP007904995:retrieved from the internet: URL: http://www2.dupont.com/Teflon_Industrial/en_US/assets/downloads/ h88800.pdf; retrieved on Jun. 19, 2008, by Authorized Officer in International Application PCT/US2008/003364, 4 pgs.

(Continued)

*Primary Examiner* — Thaddeus Cox

(57) ABSTRACT

A guide member facilitates a device swap for brachytherapy treatment. A cavity evaluation device is introduced during surgery such that a distal end of the device is disposed in a resected cavity of the patient. The cavity evaluation device includes a shaft in which is disposed an elongated guide member. In a subsequent out-patient procedure the cavity evaluation device is removed from the resected cavity. If a brachytherapy treatment is to be performed then the cavity evaluation device is removed without removing the elongated guide member such that position of a portion of the elongated guide member in the resected cavity is maintained relative to the resected cavity. An anchor member helps to maintain the position of the guide member. Introduction of a brachytherapy catheter is then facilitated by introducing the elongated guide member into an opening of the brachytherapy catheter and using the elongated guide member to guide the brachytherapy catheter to the resected cavity.

13 Claims, 9 Drawing Sheets

(51) Int. Cl.
    *A61M 25/01* (2006.01)
    *A61B 17/00* (2006.01)
(52) U.S. Cl.
    CPC .... *A61B 2017/00022* (2013.01); *A61M 25/01* (2013.01); *A61N 2005/1003* (2013.01); *A61N 2005/1008* (2013.01)
(58) Field of Classification Search
    CPC .. A61M 25/09041; A61M 2025/09058; A61M 2025/09175; A61M 2025/09183
    See application file for complete search history.

(56)  References Cited

U.S. PATENT DOCUMENTS

| | | | |
|---|---|---|---|
| 3,863,073 A | 1/1975 | Wagner | |
| 3,872,856 A | 3/1975 | Clayton | |
| 3,971,950 A | 7/1976 | Evans et al. | |
| 3,975,350 A | 8/1976 | Hudgin et al. | |
| 4,119,094 A | 10/1978 | Micklus et al. | |
| 4,160,906 A | 7/1979 | Daniels et al. | |
| 4,310,766 A | 1/1982 | Finkenzeller et al. | |
| 4,350,169 A | 9/1982 | Dutcher et al. | |
| 4,417,576 A | 11/1983 | Baran | |
| 4,454,106 A | 6/1984 | Gansow et al. | |
| 4,496,557 A | 1/1985 | Malen et al. | |
| 4,559,641 A | 12/1985 | Caugant et al. | |
| 4,571,241 A | 2/1986 | Christopher | |
| 4,690,677 A | 9/1987 | Erb | |
| 4,706,269 A | 11/1987 | Reina et al. | |
| 4,706,652 A | 11/1987 | Horowitz | |
| 4,744,099 A | 5/1988 | Huettenrauch et al. | |
| 4,754,745 A | 7/1988 | Horowitz | |
| 4,763,642 A | 8/1988 | Horowitz | |
| 4,773,086 A | 9/1988 | Fujita et al. | |
| 4,773,087 A | 9/1988 | Plewes | |
| 4,819,258 A | 4/1989 | Kleinman et al. | |
| 4,821,725 A | 4/1989 | Azam et al. | |
| 4,821,727 A | 4/1989 | Levene et al. | |
| 4,867,741 A | 9/1989 | Portnoy | |
| 4,929,470 A | 5/1990 | Rittenhouse et al. | |
| 4,969,174 A | 11/1990 | Scheid et al. | |
| 4,989,227 A | 1/1991 | Tirelli et al. | |
| 4,998,917 A | 3/1991 | Geiser et al. | |
| 4,998,930 A | 3/1991 | Lundahl | |
| 5,015,247 A | 5/1991 | Michaelson | |
| 5,018,176 A | 5/1991 | Romeas et al. | |
| RE33,634 E | 7/1991 | Yanaki | |
| 5,029,193 A | 7/1991 | Saffer | |
| 5,051,904 A | 9/1991 | Griffith | |
| 5,059,166 A | 10/1991 | Fischell et al. | |
| 5,078,142 A | 1/1992 | Siczek et al. | |
| 5,084,001 A | 1/1992 | Vant Hooft et al. | |
| 5,084,015 A | 1/1992 | Moriuchi | |
| 5,084,022 A | 1/1992 | Claude | |
| 5,106,360 A | 4/1992 | Ishiwara et al. | |
| 5,112,303 A | 5/1992 | Pudenz et al. | |
| 5,152,747 A | 10/1992 | Olivier | |
| 5,163,075 A | 11/1992 | Lubinsky et al. | |
| 5,164,976 A | 11/1992 | Scheid et al. | |
| 5,167,622 A | 12/1992 | Muto | |
| 5,199,056 A | 3/1993 | Darrah | |
| 5,199,939 A | 4/1993 | Dake et al. | |
| 5,227,969 A | 7/1993 | Waggener et al. | |
| 5,236,410 A | 8/1993 | Granov et al. | |
| 5,240,011 A | 8/1993 | Assa | |
| 5,259,847 A | 11/1993 | Trambert | |
| 5,289,520 A | 2/1994 | Pellegrino et al. | |
| 5,302,168 A | 4/1994 | Hess | |
| 5,312,356 A | 5/1994 | Engelson et al. | |
| 5,314,518 A | 5/1994 | Ito et al. | |
| 5,336,178 A | 8/1994 | Kaplan et al. | |
| 5,342,305 A | 8/1994 | Shonk | |
| 5,359,637 A | 10/1994 | Webber | |
| 5,365,562 A | 11/1994 | Toker | |
| 5,381,504 A | 1/1995 | Novack et al. | |
| 5,411,466 A | 5/1995 | Hess | |
| 5,415,169 A | 5/1995 | Siczek et al. | |
| 5,417,687 A | 5/1995 | Nardella et al. | |
| 5,422,926 A | 6/1995 | Smith et al. | |
| 5,426,685 A | 6/1995 | Pellegrino et al. | |
| 5,428,658 A | 6/1995 | Oettinger et al. | |
| 5,429,582 A | 7/1995 | Williams | |
| 5,452,367 A | 9/1995 | Bick et al. | |
| 5,465,733 A * | 11/1995 | Hinohara | A61M 25/09 600/585 |
| 5,484,384 A | 1/1996 | Fearnot | |
| 5,503,613 A | 4/1996 | Weinberger | |
| 5,506,877 A | 4/1996 | Niklason et al. | |
| 5,520,646 A | 5/1996 | D'Andrea | |
| 5,526,394 A | 6/1996 | Siczek et al. | |
| 5,535,817 A | 7/1996 | Dunne | |
| 5,539,797 A | 7/1996 | Heidsieck et al. | |
| 5,553,111 A | 9/1996 | Moore et al. | |
| 5,562,594 A | 10/1996 | Weeks | |
| 5,566,221 A | 10/1996 | Smith et al. | |
| 5,592,562 A | 1/1997 | Rooks | |
| 5,594,769 A | 1/1997 | Pellegrino et al. | |
| 5,596,200 A | 1/1997 | Sharma et al. | |
| 5,598,454 A | 1/1997 | Franetzki et al. | |
| 5,603,991 A | 2/1997 | Kupiecki et al. | |
| 5,609,152 A | 3/1997 | Pellegrino et al. | |
| 5,611,767 A | 3/1997 | Williams | |
| 5,616,114 A | 4/1997 | Thornton et al. | |
| 5,621,780 A | 4/1997 | Smith et al. | |
| 5,624,395 A | 4/1997 | Mikhail et al. | |
| 5,627,869 A | 5/1997 | Andrew et al. | |
| 5,653,683 A | 8/1997 | D'Andrea | |
| 5,657,362 A | 8/1997 | Giger et al. | |
| 5,662,580 A | 9/1997 | Bradshaw et al. | |
| 5,668,889 A | 9/1997 | Hara | |
| 5,704,926 A | 1/1998 | Sutton | |
| 5,706,327 A | 1/1998 | Adamkowski et al. | |
| 5,719,952 A | 2/1998 | Rooks | |
| 5,720,717 A | 2/1998 | D'Andrea | |
| 5,724,400 A | 3/1998 | Swerdloff et al. | |
| 5,735,264 A | 4/1998 | Siczek et al. | |
| 5,741,253 A | 4/1998 | Michaelson | |
| 5,759,173 A | 6/1998 | Preissman et al. | |
| 5,769,086 A | 6/1998 | Ritchart et al. | |
| 5,782,742 A | 7/1998 | Crocker et al. | |
| 5,800,333 A | 9/1998 | Liprie | |
| 5,803,895 A | 9/1998 | Kronholz et al. | |
| 5,803,912 A | 9/1998 | Siczek et al. | |
| 5,818,898 A | 10/1998 | Tsukamoto et al. | |
| 5,820,594 A | 10/1998 | Fontirroche et al. | |
| 5,820,717 A | 10/1998 | Siegenthaler | |
| 5,828,722 A | 10/1998 | Ploetz et al. | |
| 5,851,182 A | 12/1998 | Sahadevan | |
| 5,863,284 A | 1/1999 | Klein | |
| 5,863,285 A | 1/1999 | Coletti | |
| 5,872,828 A | 2/1999 | Niklason et al. | |
| 5,878,104 A | 3/1999 | Ploetz | |
| 5,896,437 A | 4/1999 | Ploetz | |
| 5,899,882 A | 5/1999 | Waksman et al. | |
| 5,908,406 A | 6/1999 | Ostapchenko et al. | |
| 5,913,813 A | 6/1999 | Williams et al. | |
| 5,916,143 A | 6/1999 | Apple et al. | |
| 5,919,473 A | 7/1999 | Elkhoury | |
| 5,924,973 A | 7/1999 | Weinberger | |
| 5,931,774 A | 8/1999 | Williams et al. | |
| 5,935,098 A | 8/1999 | Blaisdell et al. | |
| 5,986,662 A | 11/1999 | Argiro et al. | |
| 5,993,972 A | 11/1999 | Reich et al. | |
| 6,005,907 A | 12/1999 | Ploetz | |
| 6,013,038 A | 1/2000 | Pflueger | |
| 6,022,308 A | 2/2000 | Williams | |
| 6,022,325 A | 2/2000 | Siczek et al. | |
| 6,033,357 A | 3/2000 | Ciezki et al. | |
| 6,036,631 A | 3/2000 | McGrath et al. | |
| 6,050,930 A | 4/2000 | Teirstein | |
| 6,056,702 A | 5/2000 | Lorenzo | |
| 6,075,879 A | 6/2000 | Roehrig et al. | |
| 6,083,148 A | 7/2000 | Williams | |

(56) References Cited

U.S. PATENT DOCUMENTS

| | | |
|---|---|---|
| 6,086,970 A | 7/2000 | Ren |
| 6,091,841 A | 7/2000 | Rogers et al. |
| 6,093,142 A | 7/2000 | Ciamacco, Jr. |
| 6,095,966 A | 8/2000 | Chomenky et al. |
| 6,137,527 A | 10/2000 | Abdel-Malek et al. |
| 6,141,398 A | 10/2000 | He et al. |
| 6,143,013 A | 11/2000 | Samson et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,200,257 B1 | 3/2001 | Winkler |
| 6,216,540 B1 | 4/2001 | Nelson et al. |
| 6,217,565 B1 | 4/2001 | Cohen |
| 6,219,059 B1 | 4/2001 | Argiro |
| 6,233,473 B1 | 5/2001 | Shepherd et al. |
| 6,234,952 B1 | 5/2001 | Liprie |
| 6,243,441 B1 | 6/2001 | Zur |
| 6,248,122 B1 | 6/2001 | Klumb et al. |
| 6,251,059 B1 | 6/2001 | Apple et al. |
| 6,256,370 B1 | 7/2001 | Yavuz |
| 6,256,529 B1 | 7/2001 | Holupka et al. |
| 6,267,775 B1 | 7/2001 | Clerc et al. |
| 6,272,207 B1 | 8/2001 | Tang |
| 6,282,142 B1 | 8/2001 | Miyawaki |
| 6,289,235 B1 | 9/2001 | Webber et al. |
| 6,292,530 B1 | 9/2001 | Yavus et al. |
| 6,306,074 B1 | 10/2001 | Waksman et al. |
| 6,319,188 B1 | 11/2001 | Lovoi |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,411,836 B1 | 6/2002 | Patel et al. |
| 6,413,203 B1 | 7/2002 | Sahatjian |
| 6,413,204 B1 | 7/2002 | Winkler et al. |
| 6,415,015 B2 | 7/2002 | Nicolas et al. |
| 6,416,457 B1 | 7/2002 | Urick et al. |
| 6,416,492 B1 | 7/2002 | Nielson |
| 6,442,288 B1 | 8/2002 | Haerer et al. |
| 6,443,912 B1 | 9/2002 | Mazzola et al. |
| 6,458,069 B1 | 10/2002 | Tam et al. |
| 6,458,070 B1 | 10/2002 | Waksman et al. |
| 6,459,925 B1 | 10/2002 | Nields et al. |
| 6,482,124 B2 | 11/2002 | Winkler et al. |
| 6,482,142 B1 | 11/2002 | Winkler et al. |
| 6,501,819 B2 | 12/2002 | Unger et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,556,655 B1 | 4/2003 | Chichereau et al. |
| 6,558,390 B2 | 5/2003 | Cragg |
| 6,579,221 B1 | 6/2003 | Peterson |
| 6,597,762 B1 | 7/2003 | Ferrant et al. |
| 6,605,030 B2 | 8/2003 | Weinberger |
| 6,607,477 B1 | 8/2003 | Longton et al. |
| 6,610,013 B1 | 8/2003 | Fenster et al. |
| 6,611,575 B1 | 8/2003 | Alyassin et al. |
| 6,615,070 B2 | 9/2003 | Lee |
| 6,616,629 B1 | 9/2003 | Verin et al. |
| 6,620,111 B2 | 9/2003 | Stephens et al. |
| 6,626,849 B2 | 9/2003 | Huitema et al. |
| 6,633,674 B1 | 10/2003 | Gemperline et al. |
| 6,638,235 B2 | 10/2003 | Miller et al. |
| 6,647,092 B2 | 11/2003 | Eberhard et al. |
| 6,652,441 B2 | 11/2003 | Weinberger et al. |
| 6,673,006 B2 | 1/2004 | Winkler |
| 6,685,618 B2 | 2/2004 | Tam et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas |
| 7,322,929 B2 | 1/2008 | Lovoi |
| 7,323,692 B2 | 1/2008 | Rowlands et al. |
| 7,404,791 B2 | 7/2008 | Linares et al. |
| 7,407,476 B2 | 8/2008 | Lubock et al. |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 7,955,246 B2 | 6/2011 | Lubock et al. |
| 8,075,469 B2 | 12/2011 | Lubock et al. |
| 8,079,946 B2 | 12/2011 | Lubock et al. |
| 8,123,722 B2 | 2/2012 | Chang et al. |
| 8,137,256 B2 | 3/2012 | Cutrer et al. |
| 8,192,344 B2 | 6/2012 | Lubock et al. |
| 8,277,370 B2 | 10/2012 | Quick |
| 8,287,442 B2 | 10/2012 | Quick |
| 8,565,374 B2 | 10/2013 | Defreitas et al. |
| 9,180,312 B2 | 11/2015 | Lubock et al. |
| 9,248,311 B2 | 2/2016 | Damarati |
| 9,352,172 B2 | 5/2016 | Benson |
| 9,415,239 B2 | 8/2016 | Lubock |
| 9,579,524 B2 | 2/2017 | Damarati |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0026090 A1 | 2/2002 | Kaplan et al. |
| 2002/0045893 A1 | 4/2002 | Lane et al. |
| 2002/0050986 A1 | 5/2002 | Inoue et al. |
| 2002/0055666 A1 | 5/2002 | Hunter et al. |

(56) References Cited

U.S. PATENT DOCUMENTS

| | | |
|---|---|---|
| 2002/0075997 A1 | 6/2002 | Unger et al. |
| 2002/0095114 A1 | 7/2002 | Palasis |
| 2002/0156342 A1 | 10/2002 | Burton et al. |
| 2002/0177804 A1 | 11/2002 | Saab |
| 2002/0177870 A1* | 11/2002 | Sepetka .......... A61M 25/0113 606/194 |
| 2003/0018272 A1 | 1/2003 | Treado et al. |
| 2003/0073895 A1 | 4/2003 | Nields et al. |
| 2003/0095624 A1 | 5/2003 | Eberhard |
| 2003/0144570 A1 | 7/2003 | Hunter et al. |
| 2003/0153803 A1 | 8/2003 | Harmon |
| 2003/0191491 A1 | 10/2003 | Duane et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0015193 A1* | 1/2004 | Lamson .......... A61N 1/056 607/9 |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0087827 A1 | 5/2004 | Lubock |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0147800 A1 | 7/2004 | Barber et al. |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes et al. |
| 2005/0049521 A1 | 3/2005 | Miller et al. |
| 2005/0059990 A1 | 3/2005 | Ayala et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |
| 2005/0080313 A1 | 4/2005 | Stewart et al. |
| 2005/0101823 A1 | 5/2005 | Linares et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |
| 2005/0267320 A1 | 12/2005 | Barber et al. |
| 2005/0277577 A1 | 12/2005 | Hunter et al. |
| 2006/0014997 A1 | 1/2006 | Kindlein et al. |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0149186 A1 | 7/2006 | Wantink |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0142779 A1* | 6/2007 | Duane .......... A61M 25/0172 604/164.09 |
| 2007/0167665 A1 | 7/2007 | Hermann et al. |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1 | 1/2008 | Smith et al. |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0071212 A1 | 3/2008 | Lubock et al. |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas et al. |
| 2008/0130979 A1 | 6/2008 | Ren |
| 2008/0177127 A1 | 7/2008 | Allan et al. |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1 | 4/2009 | Edmundson |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 | 6/2009 | Chi Sing et al. |
| 2009/0171157 A1 | 7/2009 | Diedrich et al. |
| 2009/0188098 A1 | 7/2009 | Acosta et al. |
| 2009/0198095 A1 | 8/2009 | Acosta et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1 | 2/2010 | Sing et al. |
| 2010/0054400 A1 | 3/2010 | Ren |
| 2010/0069878 A1 | 3/2010 | Parsai et al. |
| 2010/0086188 A1 | 4/2010 | Ruth |
| 2010/0150306 A1 | 6/2010 | Defreitas et al. |
| 2010/0195882 A1 | 8/2010 | Ren |
| 2010/0204534 A1 | 8/2010 | Damarati |
| 2010/0204535 A1 | 8/2010 | Damarati |
| 2010/0226475 A1 | 9/2010 | Smith |
| 2010/0268029 A1* | 10/2010 | Phan .......... A61B 1/00082 600/115 |
| 2010/0286465 A1 | 11/2010 | Benson |
| 2010/0290585 A1 | 11/2010 | Eliasson |
| 2011/0069809 A1 | 3/2011 | Defreitas et al. |
| 2012/0046647 A1 | 2/2012 | Matsukuma et al. |
| 2012/0071705 A1 | 3/2012 | Lubock et al. |
| 2012/0088952 A1 | 4/2012 | Lubock et al. |
| 2012/0178983 A1 | 7/2012 | Benson |
| 2013/0225902 A1 | 8/2013 | White |
| 2017/0080252 A1 | 3/2017 | Lubock et al. |

FOREIGN PATENT DOCUMENTS

| | | |
|---|---|---|
| EP | 0536440 | 4/1993 |
| EP | 0642766 | 3/1995 |
| EP | 0693293 | 1/1996 |
| EP | 0719571 | 7/1996 |
| EP | 775467 | 5/1997 |

(56) References Cited

FOREIGN PATENT DOCUMENTS

| | | |
|---|---|---|
| EP | 0853957 | 7/1998 |
| EP | 0867200 | 9/1998 |
| EP | 0982001 | 3/2000 |
| EP | 1051990 | 11/2000 |
| EP | 1070514 | 1/2001 |
| EP | 1402922 | 3/2004 |
| EP | 1428473 | 6/2004 |
| EP | 1541188 | 6/2005 |
| EP | 1618924 | 1/2006 |
| EP | 1759637 | 3/2007 |
| JP | 10137250 | 5/1998 |
| JP | 2001120561 | 5/2001 |
| RU | 2177350 | 12/2001 |
| WO | WO 90/05485 | 5/1990 |
| WO | WO 92/10932 | 7/1992 |
| WO | WO 93/09724 | 5/1993 |
| WO | WO 9520241 | 7/1995 |
| WO | WO 9712540 | 4/1997 |
| WO | WO 97/19723 | 6/1997 |
| WO | WO 97/45053 | 12/1997 |
| WO | WO 98/16903 | 4/1998 |
| WO | WO 9815315 | 4/1998 |
| WO | WO 99/11325 | 3/1999 |
| WO | WO 99/33515 | 7/1999 |
| WO | WO 9934869 | 7/1999 |
| WO | WO 99/42163 | 8/1999 |
| WO | WO 00/51484 | 9/2000 |
| WO | WO 01/14011 | 3/2001 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 03/020114 | 3/2003 |
| WO | WO 2004/043531 | 5/2004 |
| WO | WO 2004/043535 | 5/2004 |
| WO | WO 2005/037363 | 4/2005 |
| WO | WO 2005039655 | 5/2005 |
| WO | WO 2005039665 | 5/2005 |
| WO | WO 2005/051197 | 6/2005 |
| WO | WO 2005/067442 | 7/2005 |
| WO | WO 2005110230 | 11/2005 |
| WO | WO 2005112767 | 12/2005 |
| WO | WO 2006/055830 | 5/2006 |
| WO | WO 2006/058160 | 6/2006 |
| WO | WO 2007/027831 | 3/2007 |
| WO | WO 2007/143560 | 12/2007 |
| WO | WO 2008/067557 | 6/2008 |
| WO | WO 09/079170 | 6/2009 |

OTHER PUBLICATIONS

"Essentials for life: Senographe Essential Full-Field Digital Mammography system", GE Health-care Brochure, MM-0132-05.06-EN-US, 2006, 12 pgs.

"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.

"Lorad Selenia" Document B-BI-SEO US/Intl (May 2006), copyright Hologic 2006, 12 pgs.

"Variable shield for radiation-therapy sourcewire and centering catheter", Research disclosure, Mason Publications, Hampshire, GB, vol. 438, No. 48, Oct. 2000, XP007126916, 1 page.

Abstracts of the 11th International Conference on Brain tumor Research and Therapy Oct. 31-Nov. 3, 1995, Silverado Country Club and Resort, Napa, California, Journal of Neuro-Oncology 28, p. 72, 1996, 2 pages all together.

Akagi, Y, et al.,"Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

Ashpole et al., "A New Technique of Brachytherapy for Malignant Gliomas with Caesium-137: A New Method Utilizing a Remote Afterloading System," Clinical Oncology, 1990, vol. 2, pp. 333-337.

Astrahan, Melvin A., PhD et al., "Optimization of Mammosite therapy", Int. J. Radiation Oncology Biol. Phys, vol. 58, No. 1, pp. 220-232, 2004.

Bowsher. W. G., et al., "Update on Urology-Prostate Cancer. 4-Treatment of Local Disease". European Journal of Surgical Oncology. 1995 pp. 679-682. vol. 21. No. 6.

Chan, Heang-Ping et al., "ROC study of the effect of stereoscopic imaging on assessment of breast lesions", Medica Physics, vol. 32, No. 4, Apr. 2005, 7 pgs.

Cole, Elodia, et al., "The Effects of Gray Scale Image Processing on Digital Mammography Interpretation Performance", Academic Radiology, vol. 12, No. 5, pp. 585-595, May 2005.

Cuttino, L. W., et al.,"CT-Guided Multi-Catheter Insertion Technique for Partial Breast Brachytherapy: Reliable Target Coverage and Dose Homogeneity", Brachy1herapy 4, 2005, pp. 10-17, Elsevier.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

Debicki, M. P., et al., "Localized Current Field Hyperthermia in Carcinoma of the Cervix: 3-D Computer Simulation of SAR Distribution". International Journal of Hyperthermia. 1999. pp. 427-440. vol. 15. No. 5.

Demanes, D. J . et al., "The Use and Advantages of a Multichannel Vaginal Cylinder in High-Dose-Rate Brachytherapy". Int. J. Radiation Oncology Biol. Phys. (1999). pp. 211-219. vol. 44. No. 1. Elsevier Science Inc.

Dempsey, J. F. et al., "Dosimetric Properties of a Novel Brachytherapy Balloon Applicator for the Treatment of Malignant Brain-Tumor Resection-Cavity Margins", Int. J. Radiation Oncology Biol. Phys., May 1998, pp. 421-429, vol. 42. No. 2. Elsevier.

Devic et al., "Advantages of Inflatable Multichannel Endorectal Applicator in the Neo-Adjuvant Treatment of Patients With Locally Advanced Rectal Cancer With HOR Brachytherapy", Journal of Applied Clinical Medical Physics, Spring 2005, pp. 44-49, vol. 6, No. 2.

Digital Clinical Reports, Tomosynthesis, GE Brochure 98/5493, Nov. 1998, 8 pgs.

Edmundson,Gregory K. et al., "Dosimetric Characteristics of the Mammosite RTS, a New Breast Brachytherapy Applicator", Int. J. Radiation Oncology Biol. Phys., vol. 52, No. 4, pp. 1132-1139, 2002.

Federica Pediconi et al., "Color-coded automated signal intensity-curve for detection and characterization of breast lesions: Preliminary evaluation of a new software for MR-based breast imaging", International Congress Series 1281 (2005) 1081-1086.

Fowler, J. E., "Brief Summary of Radiobiological Principles in Fractionated Radiotherapy", Seminars in Radiation Oncology, Jan. 1992, pp. 16-21, vol. 2, No. 1, W. B. Saunders Company.

Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.

Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.

Garipagaoglu, M. et al., "Geometric and Dosimetric Variations of ICRU Bladder and Rectum Reference Points in Vaginal Cuff Brachytherapy Using Ovoids", Int. J. Radiation Oncology Biol. Phys. 2004, pp. 1607-1615. Elsevier Inc.

Gaspar, L. E., et al., "Esophageal Brachytherapy", Principles and Practice of Brachytherapy, 1997, pp. 305-321, Futrua Publishing Company, Inc., Armouk, New York.

Glasgow, G. P., et al. "Remote Afterloading Technology", AAPM Report No. 41, 1993, pp. i-vi and 1-107, American Institute of Physics, Inc., 116 pgs.

Gutin, P.H. et al., "A coaxial catheter system for afterloading radioactive sources for the interstitial irradiation of brain tumors", J. Neurosur, vol. 56, pp. 734-735, 1982.

(56) References Cited

OTHER PUBLICATIONS

Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, Mar. 3, 1950.

Harada, T, et al.,"Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.

Harper, Paul V., "Some Therapeutic Applications of Radioisotopes", Journal of the Mississippi State Medical Association, Oct. 1966, vol. VII, pp. 526-533.

Hewitt, C. B., et al., "Intracavitary Radiation in the Treatment of Bladder Tumors", The Journal of Urology, vol. 107, Apr. 1972, pp. 603-606, The Williams & Wilkins Co.

Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.

Hieshima,G. B., et al. "A Detachable Balloon for Therapeutic Transcatheter Occlusions 1", Technical Notes, Jan. 1981, pp. 227-228, vol. 138.

Hine, G. J., et al., "Isodose Measurements of Linear Radium Sources in Air and Water by Means of an Automatic Isodose Recorder", The American Journal of Roentgenology and Radium Therapy, 1950, pp. 989-998, vol. 64, No. 6, The Societies.

Hoshino, T., "Brain Tumor Research Center", Abstracts of the 11th Conference on Brain Tumor Research and Therapy, Journal of Neuro-Oncology 28, 1996, pp. 31-113.

Johannesen, T.B. et al, "Intracavity Fractioned Balloon Brachytherapy in Glioblastoma", Acta Neurochir (Wien) (1999) 141: 127-133.

Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press pic.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Kolotas., C. et al., "CT Guided Interstitial High Dose Rate Brachytherapy for Recurrent Malignant Gliomas". The British Journal of Radiology. 72. (1999), pp. 805-808.

Kuettel, M. R. et al.. "Treatment of Female Urethral Carcinoma in Medically Inoperable Patients Using External Beam Irradiation and High Dose Rate Intracavitary Brachytherapy", The Journal of Urology. May 1997, pp. 1669-1671, vol. 157, The American Urological Association, Inc.

Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45, 1 page, p. 179.

Low-Beer, B. V. A., "Radioisotope Therapy", "The Clinical Use of Radioactive Isotopes", 1950, pp. 284-349, Charles C. Thomas, Publisher, Springfield, Illinois, U.S.A., See pp. 343-349.

Low-Beer, B. V. A., "The Therapeutic Use of Radioactive Isotopes", "Practical Therapeutics", Dec. 1954, pp. 69-87, vol. X, No. 6.

Mammographic Accreditation Phantom, http://www.cirsinc.com/pdfs/015cp.pdf, (2006), 2 pgs.

Marshall V. F., et al., "Current Clinical Problems Regarding Bladder Tumors", Symposium on Bladder Tumors, 1956, pp. 543-550, 9/3/May-Jun, J.B. Lippincott Co, Etc.

Micheletti, E., et al., "High-Dose-Rate Brachytherapy for Poor-Prognosis, High-Grade Glioma: (Phase II) Preliminary Results", Tumori, 1996, pp. 339-344.

Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J.B. Lippincott Company, Philadelphia.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. G0974722, Academic Press.

Nag, S., et al., "Remote Controlled High Dose Rate Brachytherapy", Critical Reviews in Oncology/Hematology 22, 1996, pp. 127-150, Elsevier Science Ireland Ltd.

Nag, S., et al., "The Future of High Dose Rate Brachytherapy", High Dose Rate Brachytherapy: A Textbook, 1994, pp. 447-453, Futura Publishing Company, Inc. , Armonk, New York 10504.

Nath, Ph.D. et al., "Development of an 241 Am Applicator for Intracavitary Irradiation of Gynecologic Cancers", I.J. Radiation Oncology Biol. Phys., May 1988, vol. 14, p. 969-978.

Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.

Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.

Russel, A.H., et al, "Intracavitary Irradiation for Carcinoma of the Urinary Bladder: Rationale, Technique, and Preliminary Results", Int. J. Radiation Oncology. Phys., 1984, pp. 215-219, vol. 10, Pergamon Press Ltd.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Slevin. N. J. et al., "Intracavitary Radiotherapy Boosting for Nasopharynx Cancer", The British Journal of Radiology, 70, Apr. 1997, pp. 412-414.

Smith, A., "Fundamentals of Breast Tomosynthesis", White Paper, Hologic Inc., WP-00007, Jun. 2008, 8 pgs.

Sneed. P. K. et al., "Interstitial Brachytherapy Procedures for Brain Tumors", Seminars in Surgical Oncology 1997; 13: 157-166. Wiley-Liss. Inc.

Stubbs, J.B., et al.,"Preclinical Evaluation of a Novel Device for Delivering Brachytherapy to the Margins of Resected Brain Tumor Cavities", J. Neurosurg 96, Feb. 2002, pp. 335-343, vol. 96.

Sylvester, J., et al., "Interstitial Implantation Techniques in Prostate Cancer", Journal of Surgical Oncology 1997; 66: 65-75. Wiley-Liss. Inc.

Symon et al., "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Tan, L. T. et al., "Radical Radiotherapy for Carcinoma of the Uterine Cervix Using External Beam Radiotherapy and a Single Line Source Brachytherapy Technique: The Clatterbridge Technique", The British Journal of Radiology, 70, Dec. 1997, pp. 1252-1258.

Tanderup et al. "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

Voung, T, et al., "High-Dose-Rate Endorectal Brachytherapy in the Treatment of Locally Advanced Rectal Carcinoma: Technical Aspects", Brachytherapy 4, 2005, pp. 230-235, Elsevier.

Walton, R. J., "Therapeutic Uses of Radioactive Isotopes in the Royal Cancer Hospital", The British Journal of Radiology, 1950, pp. 559-599, William Heinemann, Publisher.

(56) References Cited

OTHER PUBLICATIONS

Walton, R. J., et al., Radioactive Solution (24Na and 82 Br) in the Treatment of Carcinoma of the Bladder:, British Medical Bulletin, 1952, pp. 158-165, Medical Dept., The British Council.
Wang, C. C., "Carcinoma of the Nasopharynx", Radiation Therapy of Head and Neck Neoplasms, 1997, pp. 257-280, Chapter 10, Wiley-Liss, Inc.
Wheeler, F.W. et al. (2006), "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Wu, Tao et al., "Tomographic mammography using a limited number of low-dose cone-beam images", Medical Physics, AIP, Melville, NY, vol. 30, No. 3, Mar. 1, 2003, pp. 365-380.
Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.
Yin, W., "Brachytherapy of Carcinoma of the Esophagus in China, 1970-1974 and 1982-1984", Brachytherapy HOR and LOR, May 4-6, 1989, pp. 52-56.

\* cited by examiner

USING A GUIDED MEMBER TO FACILITATE BRACHYTHERAPY DEVICE SWAP

CROSS REFERENCE TO RELATED APPLICATIONS

This application is a continuation of and claims the benefit of priority of U.S. application Ser. No. 12/894,888, filed Sep. 30, 2010, now U.S. Pat. No. 9,352,172, entitled "Using a Guide Member to Facilitate Brachytherapy Device Swap", the disclosure of which is hereby incorporated by reference herein.

BACKGROUND OF THE INVENTION

The present invention is generally related to medical treatments, and more particularly to interstitial Brachytherapy. Malignant tumors are often treated by surgical resection to remove as much of the tumor as possible. Radiation therapy can then be used to target the residual tumor margin. The radiation therapy can be administered through various methods including external-beam radiation, stereotactic radiosurgery, and permanent or temporary brachytherapy.

Brachytherapy is a radiation therapy in which a source of therapeutic rays is inserted into the body at or near a tumor or other proliferative tissue disease site. At least one breast brachytherapy radiation treatment begins with insertion of a cavity evaluation device into the resected cavity during the lumpectomy procedure. If it is later determined that the patient is to be given brachytherapy treatment then the cavity evaluation device is removed during an office visit and a brachytherapy catheter is inserted into the path through the tissue previously occupied by the cavity evaluation device. More particularly, the catheter shaft is inserted into the tissue so that a balloon disposed at the distal end of the shaft is positioned within the resected cavity. The balloon is then inflated and radioactive material is loaded into one or more lumens for delivery via the brachytherapy catheter. The brachytherapy catheter is removed upon completion of the treatment.

SUMMARY OF THE INVENTION

The present invention is predicated in-part on recognition that introducing a device such as a brachytherapy catheter into a path previously occupied by a device such as a cavity evaluation device can be difficult to perform as an outpatient procedure. Because the path is through soft tissue it can close rapidly and does not always accurately guide the brachytherapy catheter to the resected cavity.

In accordance with an aspect of the invention, a method for facilitating brachytherapy treatment comprises the steps of: positioning a first device such that a distal end of the first device is disposed in a resected cavity of the patient, the first device including a shaft in which is disposed an elongated guide member; removing the first device from the resected cavity without removing the elongated guide member such that position of a portion of the elongated guide member in the resected cavity is maintained relative to the resected cavity; and introducing a brachytherapy catheter by introducing the elongated guide member into an opening of the brachytherapy catheter and using the elongated guide member to guide the brachytherapy catheter to the resected cavity.

In accordance with another aspect of the invention, apparatus for facilitating brachytherapy treatment comprises: a shaft; a tip disposed at a first end of the shaft; an inflatable member disposed around the shaft; an inflation lumen which transfers fluid into and out of the inflatable member; and an opening in the tip which receives a separate elongated guide member, and via which the guide member can be introduced to soft tissue.

In accordance with another aspect of the invention, apparatus for facilitating brachytherapy treatment comprises: a shaft; a tip disposed at a first end of the shaft; an inflatable member disposed around the shaft; an inflation lumen which transfers fluid into and out of the inflatable member; at least one dosing lumen; and an opening in the tip which receives a separate elongated guide member, and through which the guide member slidably moves in order to guide the apparatus through soft tissue.

One advantage of the guide member is that it helps to guide the brachytherapy catheter to the resected cavity. Furthermore, the guide member helps to accurately position the brachytherapy catheter and associated dosing lumens within the resected cavity.

DETAILED DESCRIPTION

Figure 1:
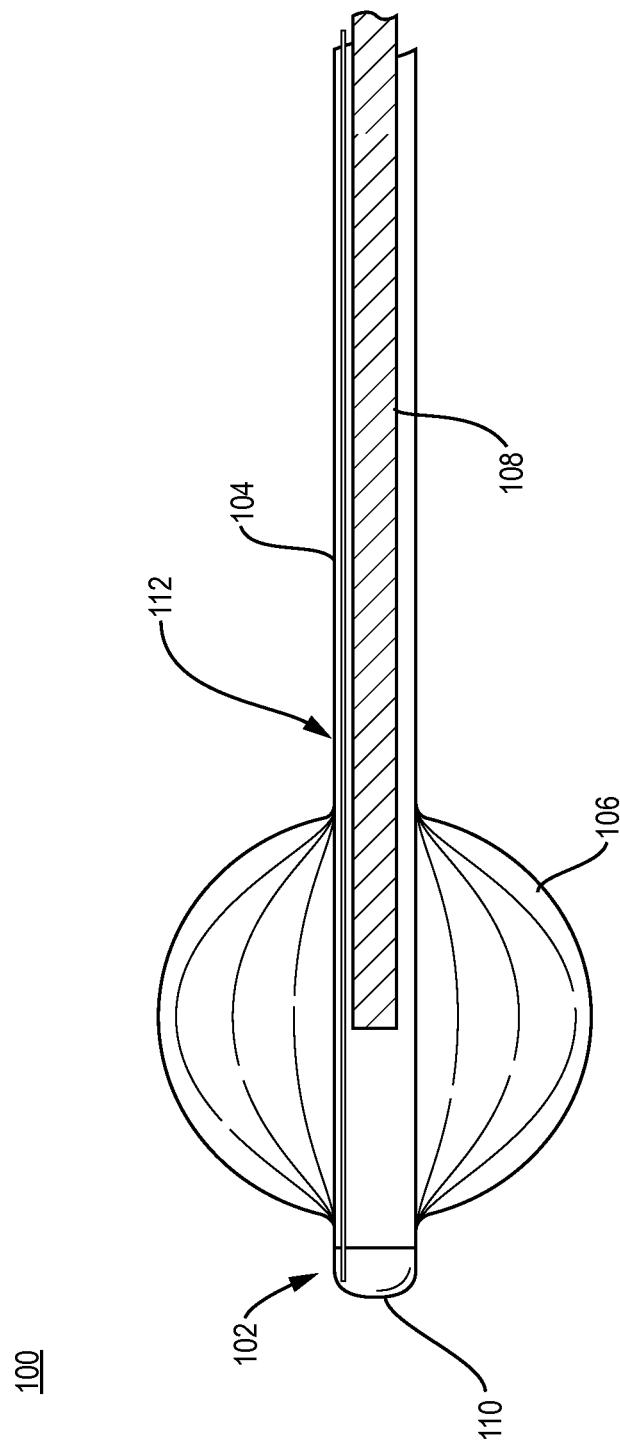
FIG. 1 illustrates a cavity evaluation device adapted to introduce a guide member.

FIG. 1 illustrates a medical device 100 adapted to introduce a guide member 102 into soft tissue to facilitate swapping of medical devices associated with a treatment such as interstitial brachytherapy, e.g., swapping a cavity evaluation device for a brachytherapy catheter. Device 100 may be a type of cavity evaluation device which includes a shaft 104, hub 110, inflatable member 106, inflation lumen 108, and a tubular opening or lumen 112 for a separate guide member 102. The shaft is characterized by a proximal end (hub) and a distal end (tip 110). The inflation lumen is coupled at the proximal end to a connector (not illustrated). Once the device is positioned within the resected cavity the inflatable member is inflated, which helps maintain the device in position.

Figure 2:
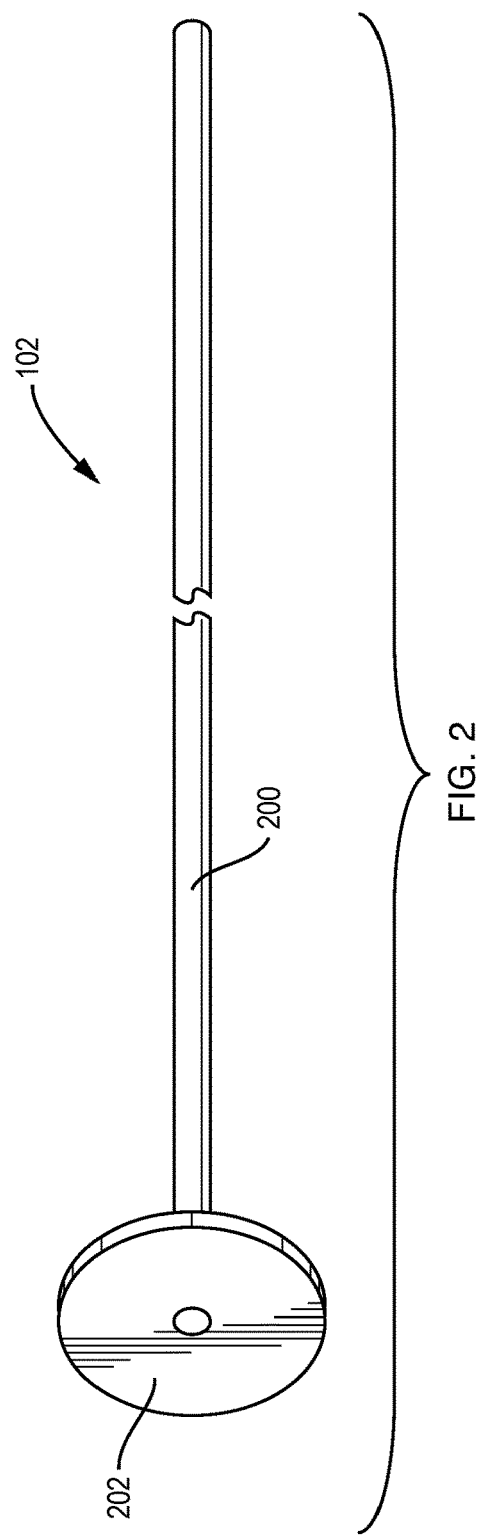
FIG. 2 illustrates an embodiment of a guide member.
Figure 3:
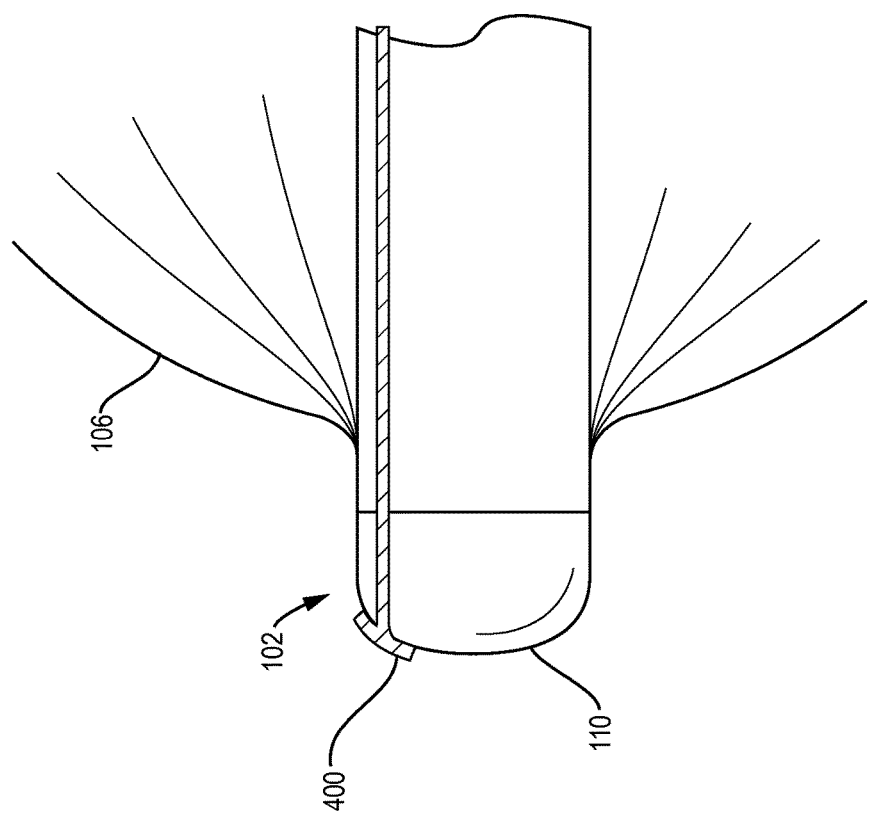
FIGS. 3 and 4 illustrate an alternative embodiment of the cavity evaluation device and guide member.
Figure 4:
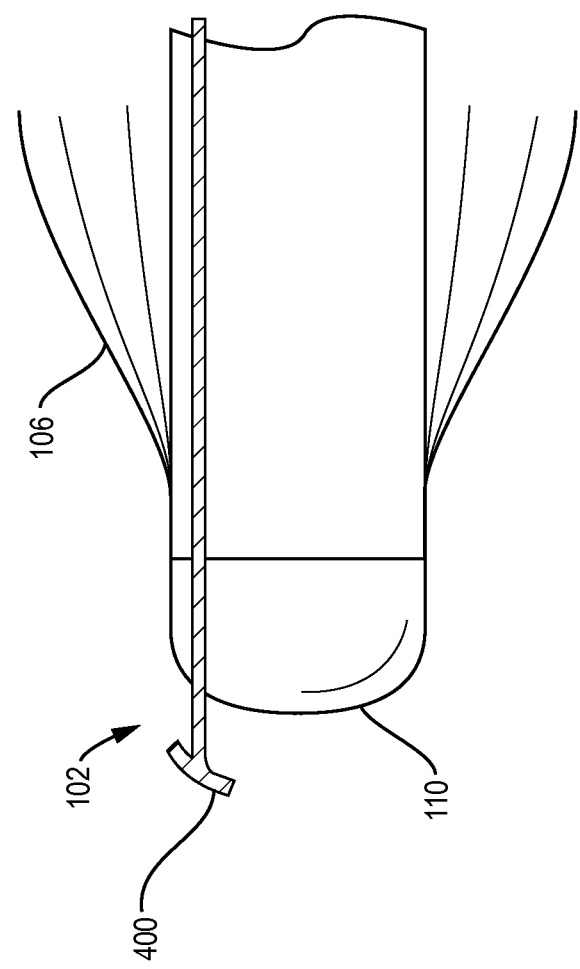
Figure 5:
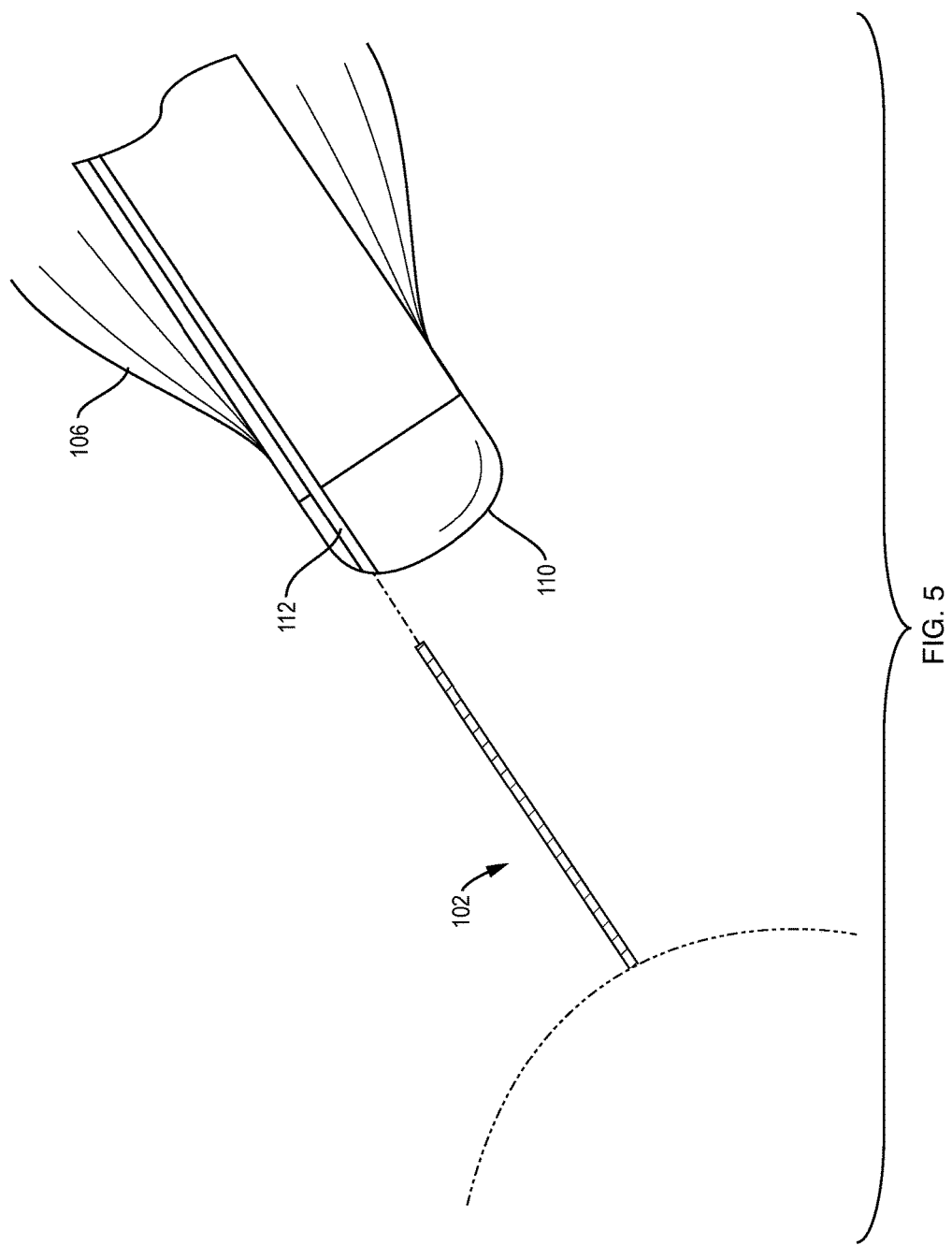
FIG. 5 illustrates withdrawal of the cavity evaluation device while guide member position is maintained.

Referring to FIGS. 1 and 2, an opening in the tip 110 at the distal end of the shaft enables the elongated guide member 102 to be slidably moved into and out of the shaft 104. More particularly, the guide member 102 slides into or out of the tubular opening 112 formed in the shaft or a lumen disposed in the shaft. The guide member 102 includes a guide wire 200 and may also include an anchor member 202 at its distal end. The anchor member 202 helps to maintain the guide member 102 in a fixed position relative to surrounding tissue following introduction. This is accomplished by increasing resistance against the surrounding tissue to inhibit movement. The guide wire 200 and anchor member 202 may be made from a flexible material including but not limited to metallics such as nickel titanium (Nitinol), polyurethane, nylon, Polyether Block Amide (PEBA), Low-density polyethylene (LDPE), thermoplastic polyester elastomers, or PolyEtherEther-Ketone (PEEK). In one embodiment the guide wire and anchor member are imagable via various modalities based on sonic, electromagnetic or magnetic resonance imaging techniques. In the illustrated embodiment the anchor member 202 is disk-shaped and the guide wire 200 is attached at the center of the anchor member approximately perpendicular to a plane defined by the anchor member. However, those skilled in the art will recognize that the anchor member could have any of various alternative shapes and types of connection to the guide wire. For example, and without limitation, an anchor member 400 (FIGS. 3 and 4) may be characterized by a curvature that matches the portion of the tip 110 against which the anchor member will be disposed when loaded into device 100.

Referring now to FIGS. 1 through 6, the device 100 is pre-loaded with a guide member 102 before being introduced during the lumpectomy procedure. More particularly, the guide member 102 is introduced such that the distal end and inflatable member 106 are positioned within the resected cavity. Imaging equipment may be utilized to facilitate proper positioning. The inflatable member is then inflated by coupling the device to a source of pressurized fluid via connector. The inflation fluid flows into the inflatable member via the inflation lumen 108. One or more inflation holes (not shown) extend through the inflation lumen into the inflatable member. Once inflated, the inflatable member 106 helps to maintain the position of the device 100 with respect to the resected cavity. The connector is then detached from the fluid source and the device is left in place.

If it is later determined that the patient is to be given brachytherapy treatment then the device 100 is removed during an office visit and a brachytherapy catheter 600 with an inflatable member 602, such as a balloon, mounted on its distal end is inserted into the track through the tissue previously occupied by the cavity evaluation device 100. More particularly, the inflatable member 106 is deflated and the cavity evaluation device 100 is removed while the position of the guide member 102 relative to the resected cavity is maintained. Deployment of the guide member by creating separation between the anchor member 202 and the tip 110 (see FIG. 4) can help maintain the position of the guide member 102 during removal of the cavity evaluation device by, for example, preventing the anchor member from inadvertently latching onto or adhering to the tip. The guide member 102 may be deployed either before or after deflation of the inflatable member 106 by pushing on a free end of the guide wire. In either case, the inflatable member is deflated in order to permit removal of the cavity evaluation device. A portion of the guide wire 200 may extend out from the body of the patient following complete removal of the cavity evaluation device 100 in order to facilitate insertion of the guide wire into a receiver of the brachytherapy catheter shaft. It will be appreciated that the cavity evaluation device can alternatively be removed without deploying the guide member, i.e., removed along with the guide member, if necessary or desirable.

Figure 6:
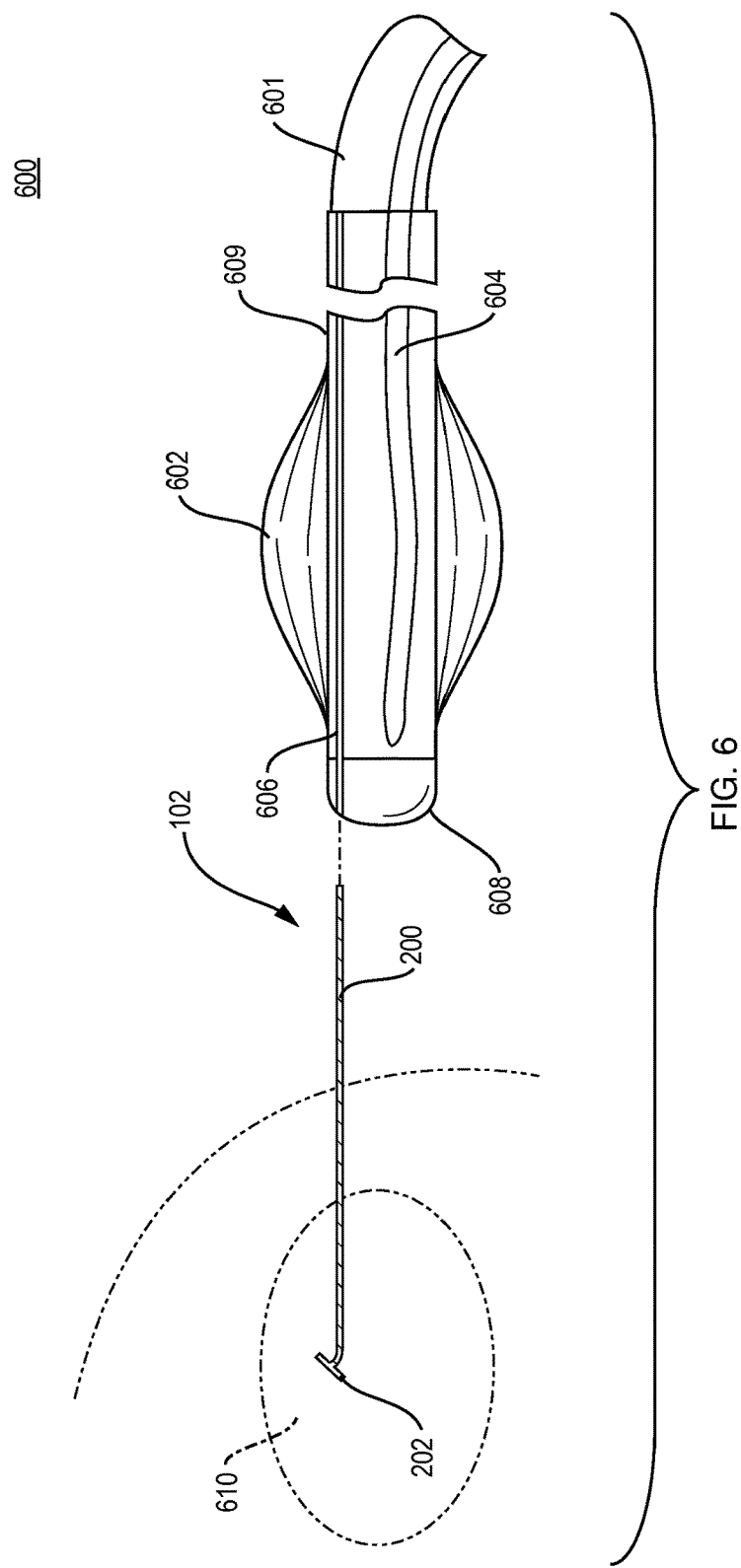
FIG. 6 illustrates use of a brachytherapy catheter adapted to utilize the guide member.

Referring now to FIG. 6, a flexible brachytherapy catheter 600 includes a flexible shaft 601, an inflatable member 602, at least one flexible dosing lumen 604, an inflation lumen (not illustrated), a guide lumen or tubular opening (collectively 606), a tip 608 and rigid section 609. Each dosing lumen 604 is sized to accommodate one or more radiation sources. The inflation lumen is coupled at a proximal end to a connector for introducing fluid for inflation. The lumens are made, for example, from a flexible material such as polyurethane, Nylon, Pebax, LDPE, Hytrel, or PEEK. Each dosing lumen 604 slidably extends through the flexible shaft and into openings which extend longitudinally into the rigid section 609. The openings in the rigid section are sized so that the exterior of each dosing lumen is tightly received in its respective opening. The lumens may be fixedly attached to the rigid section using an adhesive. The inflatable member functions in the same manner as the inflatable member of the device 100.

With the guide member 102 deployed (i.e. separated from the cavity evaluation device 100) and the device 100 removed from the patient, the guide wire 200 is used to facilitate introduction of the brachytherapy catheter device 600 by guiding the catheter through the existing opening in the soft tissue. As indicated above, the catheter shaft 601 includes a tip 608 with at least one opening 606 sized to receive the guide wire. Once inserted into the opening in the tip, the guide wire 200 is received by the associated lumen or tubular opening 606 as the brachytherapy catheter 600 is inserted into the soft tissue. Those skilled in the art will recognize that the flexibility of the guide wire 200 and resistance presented by the anchor member 202 in the soft tissue may be adjusted to achieve a desired result for a particular type of soft tissue, e.g., to present suitable resistance against movement. For example, the anchor member could be inflatable. The brachytherapy catheter 600 is eventually moved slidably along the guide wire to the extent that the tip 608 of the brachytherapy catheter contacts the anchor member 202, thereby indicating completion of that part of the procedure and helping to assure proper positioning of the brachytherapy catheter and associated dosing lumens with respect to the resected cavity 610. The inflatable member 602 is inflated after the tip of the catheter contacts the anchor member. The dosing lumens 604 are then used to deliver radiation therapy as already known in the art. The guide member 102 may be removed along with the brachytherapy catheter 600 once the treatment is completed. Alternatively, the guide member may be left in place if desired.

Figure 7:
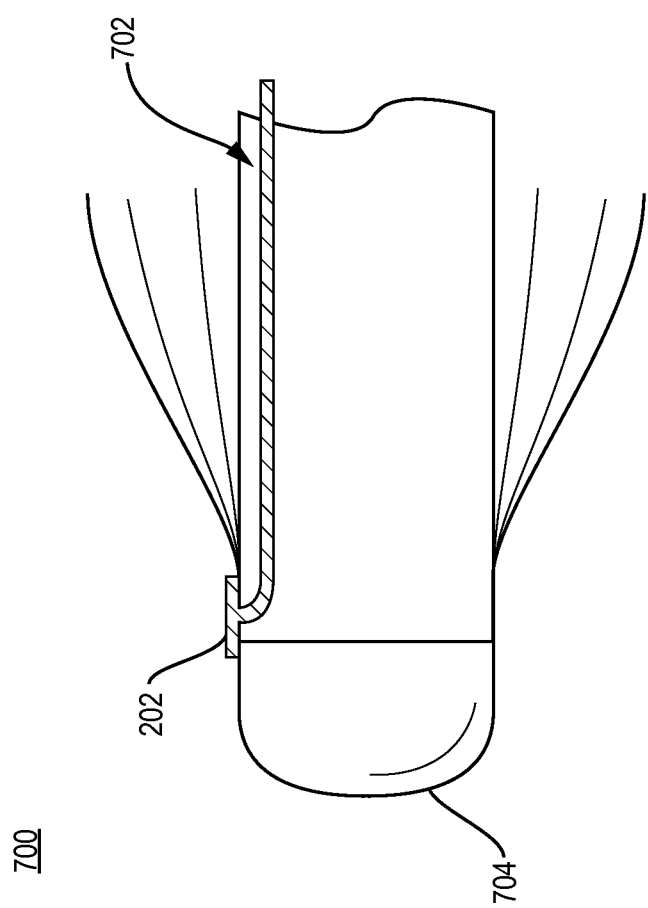
FIG. 7 illustrates an alternative embodiment of the cavity evaluation device or brachytherapy catheter.

FIG. 7 illustrates an alternative embodiment of the cavity evaluation device or brachytherapy catheter (collectively 700). In this alternative embodiment the device 700 includes a non-linear lumen or tubular opening 702 for receiving the guide wire. More particularly, the lumen or tubular opening is characterized by an arcuate turn through approximately 90 degrees such that the anchor member 202 is disposed against a side of the tip 704. One advantage of this embodiment is that the anchor member does not cover the portion of the tip where channels for lumens may be placed.

Figure 8:
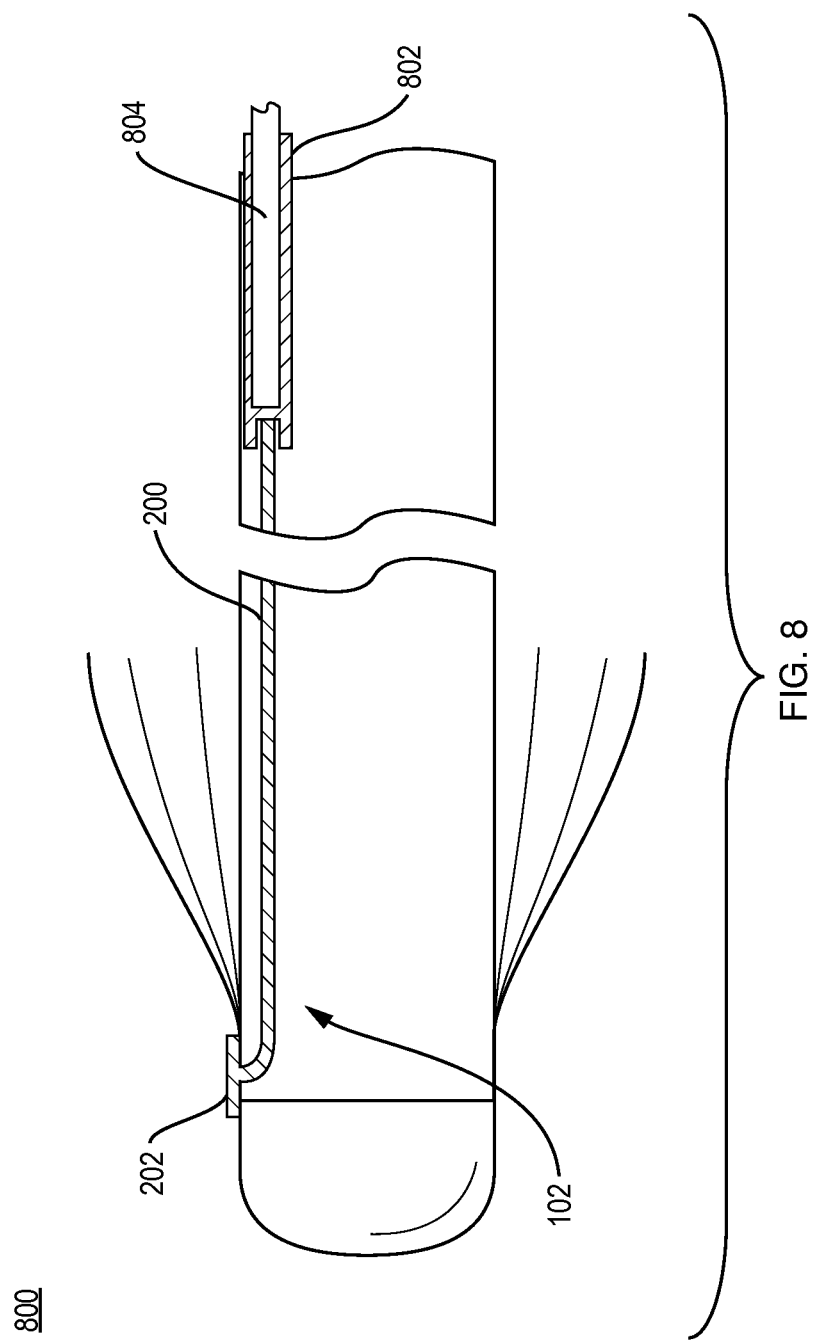
FIGS. 8 and 9 illustrate apparatus for facilitating introduction of the guide member and prevention of contamination.
Figure 9:
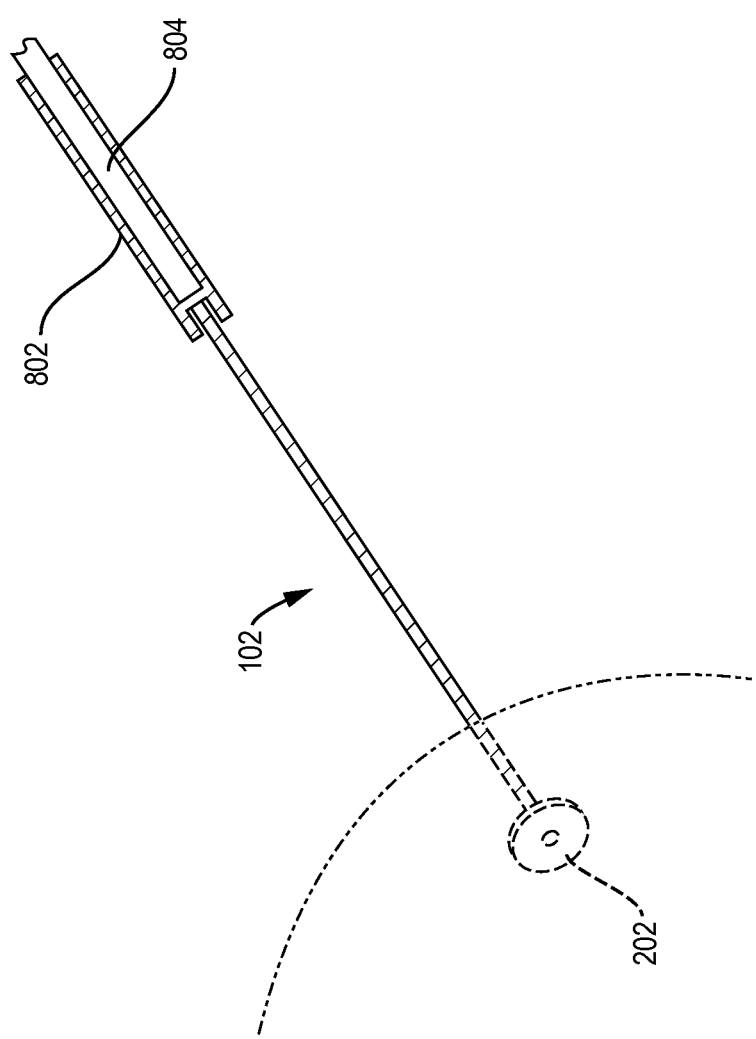

FIGS. 8 and 9 illustrate apparatus for facilitating introduction of the guide member and prevention of contamination. As described above, proper positioning of the anchor member 202 facilitates proper positioning of the brachytherapy catheter 600 and dosing lumens 604. Because soft tissue may present relatively little resistance to removal of the guide member 102 during withdrawal of the cavity evaluation device 100, a separate tool 800 may be used to apply force against the free end of the guide wire 200 as the cavity evaluation device is withdrawn. The tool 800 may include an outer sheath 802 in which a push wire 804 is disposed. The free end of the guide wire is threaded into the sheath and pressure is applied against the guide wire by means of the push wire as the cavity evaluation device is withdrawn. Note that this helps to prevent both movement of the anchor member and contamination of the free end of the guide wire. Moreover, the sheath may be capped and remain in place following removal of the cavity evaluation device and push wire in order to help prevent contamination if the cavity evaluation tool will not be immediately replaced with the brachytherapy catheter.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. An apparatus for facilitating brachytherapy treatment comprising:
    an elongated guide member comprising a guide wire and a non-inflatable anchor member at a distal end of the guide wire, wherein the non-inflatable anchor member comprises a curvature; and
    a device comprising:
        a shaft defining a lumen configured to slidably receive the elongated guide member;
        a tip disposed at a first end of the shaft, wherein the tip comprises an outer curvature configured to mate with the non-inflatable anchor curvature when the elongated guide member is received in the lumen;
        an inflatable member disposed around the shaft;
        an inflation lumen which transfers fluid into and out of the inflatable member; and
        an opening in the tip which receives the elongated guide member, and via which the elongated guide member can be introduced to soft tissue, wherein the opening is sized so as to receive all but the non-inflatable anchor member of the elongated guide member.

2. The apparatus of claim 1 further including a dosing lumen disposed in the shaft to receive a radiation source.

3. The apparatus of claim 1 wherein the non-inflatable anchor member curvature is contoured to match the tip outer curvature against which the non-inflatable anchor member is disposed when the guide wire is loaded into the shaft.

4. The apparatus of claim 3 wherein the opening in the tip is through a side of the tip.

5. The apparatus of claim 3 wherein the opening in the tip is through a most distal portion of the tip.

6. The apparatus of claim 3 further including a sheath disposed around a free end of the guide wire.

7. The apparatus of claim 6 further including a push wire inserted into the sheath to apply force against the free end of the guide wire.

8. The apparatus of claim 1, wherein the shaft comprises a rigid portion and a flexible portion and wherein the inflatable member is disposed about the rigid portion.

9. The apparatus of claim 1, wherein the device is a brachytherapy catheter.

10. The apparatus of claim 1, wherein the device is a cavity evaluation device.

11. The apparatus of claim 1, wherein the opening is defined by the tip of the shaft.

12. The apparatus of claim 1, wherein the opening is defined by a side surface of the shaft.

13. The apparatus of claim 1, wherein the lumen is defined by a portion of the shaft that is off-center of the shaft.

* * * * *